United States Patent [19]

Avar et al.

[11] 4,029,684
[45] June 14, 1977

[54] 2-HYDROXYBENZOPHENONE DERIVATIVES

[75] Inventors: Lajos Avar, Binnigen; Kurt Hofer, Muchenstein, both of Switzerland

[73] Assignee: Sandoz Ltd., Basel, Switzerland

[22] Filed: May 16, 1975

[21] Appl. No.: 578,108

Related U.S. Application Data

[63] Continuation of Ser. No. 377,749, July 9, 1973, abandoned.

[52] U.S. Cl. .................. 260/439 R; 260/45.85 B; 260/45.75 R; 260/45.75 C; 260/45.75 N; 260/45.75 F; 260/45.75 V; 260/45.75 W; 260/45.9 R; 260/45.95 F; 260/429 R; 260/429.5; 260/429.9; 260/435 R; 260/438.1; 260/465 F; 260/469; 260/517

[51] Int. Cl.² .................. C07C 69/88; C07F 7/24; C07F 1/04; C07F 15/04

[58] Field of Search ........ 260/473 S, 429 R, 429.5, 260/429.9, 435 R, 438.1, 439

[56] References Cited

UNITED STATES PATENTS

| | | | |
|---|---|---|---|
| 2,898,323 | 8/1959 | Clark | 260/473 S |
| 3,072,602 | 1/1963 | Clark et al. | 260/473 S |
| 3,206,431 | 9/1965 | Doyle et al. | 260/473 S |

FOREIGN PATENTS OR APPLICATIONS 1,936,280    1/1970    Germany

*Primary Examiner*—Paul J. Killos
*Attorney, Agent, or Firm*—Gerald D. Sharkin; Richard E. Vila; Thomas C. Doyle

[57] ABSTRACT

The present invention concerns novel 2-hydroxybenzophenone derivatives and metal complexes thereof of the formula:

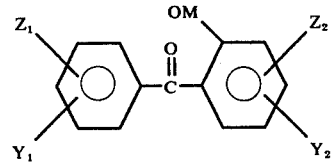

wherein $Z_1$, $Z_2$, $Y_1$ and $Y_2$ are each, independently, hydrogen or a substituent, at least one of $Y_1$ and $Y_2$ being a group

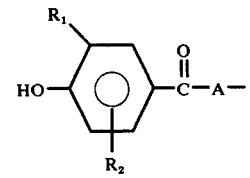

wherein, $R_1$ is alkyl
$R_2$ is hydrogen or a substituent and
A is oxygen, sulphur or

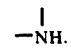

The compounds are useful for stabilizing organic material, e.g. plastics, against degradation under the influence of U.V. radiation.

9 Claims, No Drawings

2-HYDROXYBENZOPHENONE DERIVATIVES

This is a continuation, application Ser. No. 377,749 filed July 9, 1973, and now abandoned.

The present invention relates to aromatic compounds and more specifically to 2-hydroxybenzophenone derivatives and metal complexes thereof, suitable for stabilizing organic materials against degradation under the influence of ultraviolet radiation, such compounds being hereinafter referred to as U.V. stabilizers.

Accordingly, the present invention provides compounds of formula I,

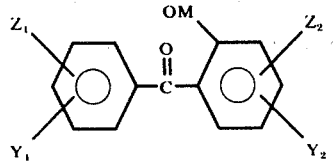

wherein $Z_1$ and $Z_2$ are each, independently, hydrogen halogen, hydroxyl, —CN, —COOH, alkyl($C_1$–$C_{12}$), phenyl, mono- or di- alkyl($C_1$–$C_8$) substituted phenyl, a group —X-R or a group —COOR, wherein X is oxygen, sulphur,

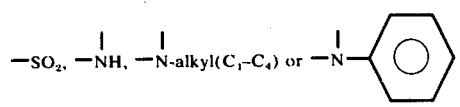

and

R is alkyl($C_1$–$C_{12}$), cycloalkyl-($C_5$–$C_{12}$), cycloalkyl($C_5$–$C_{11}$)-alkyl($C_1$–$C_7$), mono-, di- or tri- alkyl($C_1$–$C_4$) ring substituted cycloalkyl($C_5$–$C_{12}$) or cycloalkyl($C_5$–$C_{11}$)alkyl($C_1$–$C_7$), aralkyl($C_7$–$C_{12}$), phenyl, or aralkyl($C_7$–$C_{12}$) or phenyl substituted on the aryl nucleus by 1 or 2 alkyl($C_1$–$C_6$) groups, $Y_1$ and $Y_2$, each have, independently, the significances of $Z_1$ and $Z_2$ or

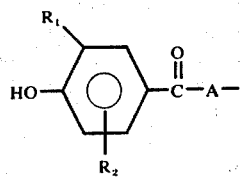

wherein $R_1$ is tertiary alkyl($C_4$–$C_9$)

$R_2$ is hydrogen, alkyl ($C_1$–$C_{18}$), cycloalkyl($C_5$–$C_{12}$), cycloalkyl($C_5$–$C_{11}$)alkyl($C_1$–$C_7$), cycloalkyl($C_5$–$C_{12}$) or cycloalkyl($C_5$–$C_{11}$)alkyl($C_1$–$C_7$) mono-, di- or tri- ring substituted by alkyl($C_1$–$C_4$), aralkyl($C_7$–$C_{12}$) or aralkyl($C_7$–$C_{12}$) mono- or di- substituted on the aryl nucleus by alkyl ($C_1$–$C_6$), and A is oxygen, sulphur or

wherein at least one $Y_1$ and $Y_2$ is a group

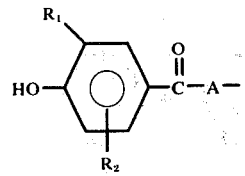

wherein $R_1$, $R_2$ and A are as defined above, and

M is hydrogen or one equivalent of a divalent metal cation.

It is to be understood that by the term "halogen" as used herein is meant fluorine, chlorine or bromine.

A preferred group of compounds of formula I are the compounds of formula Ia,

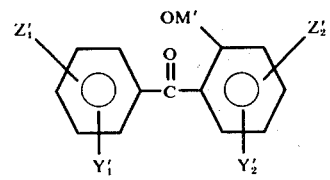

wherein $Z_1'$ and $Z_2'$ are each, independently, hydrogen, halogen, alkyl($C_1$–$C_6$), phenyl, phenyl mono- or di-substituted by alkyl($C_1$–$C_6$), or a group —X'-R', wherein X' is oxygen, sulphur or —$SO_2$ and R' is alkyl($C_1$–$C_6$), phenyl, or phenyl mono substituted by alkyl($C_1$–$C_6$), $Y_1'$ and $Y_2'$ each have, independently, the significances of $Z_1'$ and $Z_2'$ or

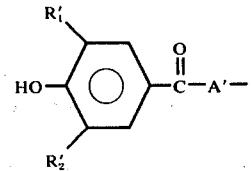

wherein $R_1'$ is tertiary alkyl($C_4$–$C_6$), $R_2'$ is hydrogen or alkyl($C_1$–$C_6$) and A' is oxygen or

wherein at least one of $Y_1'$ and $Y_2'$ is

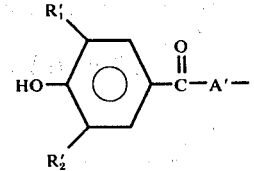

wherein $R_1'$, $R_2'$ and A' are as defined above and

M' is hydrogen or one equivalent of divalent nickel, zinc, manganese, copper, cobalt, lead, titanium or calcium.

A further preferred group of compounds of formula I are the compounds of formula Ib,

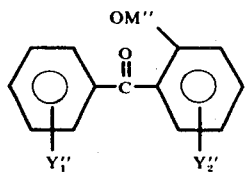

Ib wherein $Y_1''$ and $Y_2''$ are each, independently, hydrogen, halogen, alkyl($C_1$–$C_4$), phenyl, phenyl mono substituted by alkyl($C_1$–$C_4$), a group —X''-R'' wherein X'' is oxygen or —$SO_2$ and

R'' is alkyl($C_1$–$C_4$), phenyl, or phenyl mono substituted by alkyl($C_1$–$C_4$), or a group

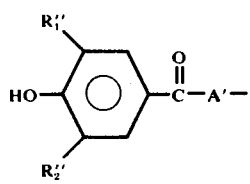

wherein $R_1''$ is tertiary butyl, $R_2''$ is branched alkyl($C_3$–$C_6$), and

A' is as defined above, wherein at least one of $Y_1''$ and $Y_2''$ is

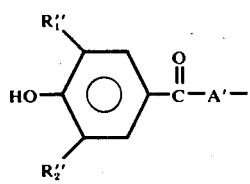

wherein $R_1''$, $R_2''$ and A' are as defined above, and

M'' is hydrogen or one equivalent of divalent nickel or manganese.

A further preferred group of compounds of formula I are the compounds of formula Ic,

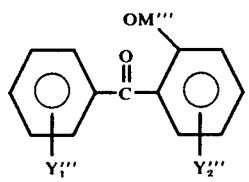

Ic wherein $Y_1'''$ and $Y_2'''$ are each, independently, hydrogen, halogen, alkyl($C_1$–$C_4$), phenyl, phenyl mono substituted by alkyl($C_1$–$C_4$), a group —X''-R'', wherein X'' and R'' are as defined above, or a group

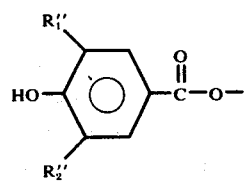

wherein $R_1''$ and $R_2''$ are as defined above, wherein at least one of $Y_1'''$ and $Y_2'''$ is

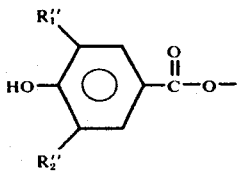

wherein $R_1''$ and $R_2''$ are as defined above, and

M'''' is hydrogen or one equivalent of divalent nickel.

Another group of preferred compounds of formula I are the compounds of formula Id

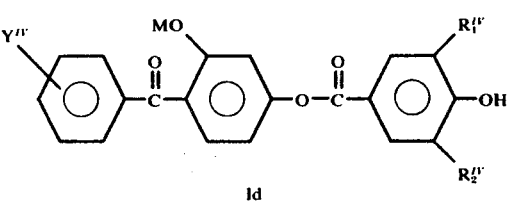

Id wherein $Y^{IV}$ is hydrogen, halogen, alkyl($C_1$–$C_9$), alkoxy ($C_1$–$C_9$), alkylsulphonyl($C_1$–$C_9$), phenyl, phenoxy, phenylsulphonyl or a group

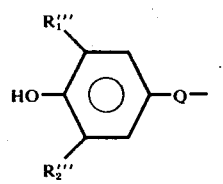

wherein $R_1'''$ is tertiary alkyl($C_4$–$C_9$), especially tertiary butyl, $R_2'''$ is hydrogen or alkyl($C_1$–$C_9$), particularly branched alkyl($C_3$–$C_9$), especially tertiary alkyl(-$C_4$–$C_9$), e.g. tertiary butyl,

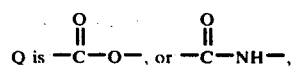

Q is $-\overset{O}{\underset{\|}{C}}-O-$, or $-\overset{O}{\underset{\|}{C}}-NH-$, $R_1^{IV}$ is tertiary alkyl($C_4$–$C_9$), especially tertiary butyl, $R_2^{IV}$ is hydrogen or alkyl($C_1$–$C_9$), particularly branched alkyl($C_3$–$C_9$), especially tertiary alkyl(-$C_4$–$C_9$), e.g. tertiary butyl, and M is as defined above, preferably having the significances of M', more preferably having the significances of M'', especially M''''.

Another group of preferred compounds of formula I are the compounds of formula Ie,

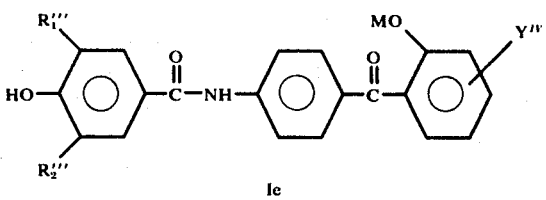

Ie wherein $R_1'''$, $R_2'''$, M and $Y^{IV}$ are as defined above, particularly the compounds wherein $Y^{IV}$ is hydrogen, alkyl($C_1$–$C_9$) or alkoxy($C_1$–$C_9$).

When any of $Z_1$, $Z_2$, $Y_1$ or $Y_2$, or where appropriate, their counterparts in formulae Ia, Ib, Ic, Id or Ie, are or contain alkyl, e.g. alkyl, alkoxy, alkylthio or alkylsulphonyl, this may be straight or branched chain, primary, secondary or tertiary. Examples of groups embraced by the term alkyl are the primary alkyl groups methyl, ethyl, n-propyl, n-butyl, n-pentyl and n-hexyl, the secondary alkyl groups isopropyl, 2-butyl, 3-methyl-2-butyl, 3-hexyl, 2-methyl-3-pentyl, 4-heptyl, 2-methyl-3-hexyl and 4-octyl, and the tertiary alkyl groups tertiary butyl and 2-methyl-2-butyl. Examples of branched alkyl are 2-methyl-1-propyl, 2,2-dimethyl-1-propyl, 2-methyl-1-butyl, 2-ethyl-1-butyl, 2,2-dimethyl-1-butyl, 2-methyl-1-pentyl and 3-methyl-1-pentyl.

When any of $Z_1$, $Z_2$, $Y_1$ or $Y_2$ are cycloalkyl or alkylcycloalkyl, examples thereof are cyclopentyl, cyclohexyl, cycloheptyl, 2,3- or 4-methylcyclohexyl, cyclooctyl, 2,5-, 2,6-, 3,5-dimethylcyclohexyl, 2-propylcyclohexyl and 3,3,5-trimethyl-cyclohexyl. Preferred are cycloalkyl and alkylcycloalkyl having 5,6 or 7 ring carbon atoms, particularly cyclohexyl and alkylcyclohexyl.

When any of $Z_1$, $Z_2$, $Y_1$ or $Y_2$ are cycloalkylalkyl, this is preferably of 7 to 12 carbon atoms in the aggregate thereof, and preferably contains 5,6 or 7, particularly 6 ring carbon atoms. Examples of cycloalkylalkyl are cyclohexyl-methyl, 2-cyclohexylethyl, cycloheptyl-methyl and 3-cyclohexyl-propyl.

When any of $Z_1$, $Z_2$, $Y_1$ or $Y_2$, or where appropriate, their counterparts in formulae Ia, Ib, Ic, Id and Ie, are halogen, this is preferably chlorine.

When any of $Z_1$, $Z_2$, $Y_1$ or $Y_2$ are aralkyl, then the aryl portion thereof may, for example, be phenyl or naphthyl. Preferably, aralkyl contains from 7 to 12 carbon atoms and the aryl portion thereof is phenyl. Preferred examples of aralkyl groups are benzyl and 2-phenylethyl.

Preferably one, or more preferably both, of the groups $Y_1$ and $Y_2$, or where appropriate, their counterparts in formulae Ia, Ib, Ic, Id and Ie, occupy the 4 or as the case may be 4', position of the benzophenone nucleus.

The present invention also provides a process for the production of a compound of formula I, which comprises a. condensing a compound of formula III,

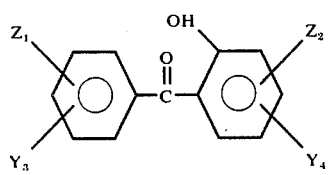

wherein $Z_1$ and $Z_2$ are as defined above and
$Y_3$ and $Y_4$ each have, independently the significances of $Z_1$ and $Z_2$, or —AH
wherein A is as defined above,
wherein at least one of $Y_3$ and $Y_4$ is —AH,
wherein A is as defined above, with a compound of formula IV,

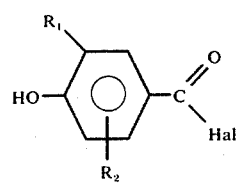

wherein $R_1$ and $R_2$ are as defined above, and
Hal is chlorine or bromine, or b. condensing a compound of formula IIIa

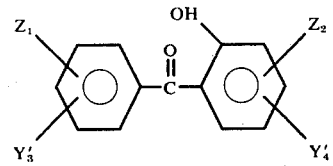

wherein $Z_1$ and $Z_2$ are as defined above and
$Y_3'$ and $Y_4'$ each have, independently the significances of $Z_1$ and $Z_2$, or —A''-H,
wherein A'' is oxygen or sulphur,
wherein at least one of $Y_3'$ and $Y_4'$ is —A''-H,
wherein A'' is as defined above, with a compound of formula V,

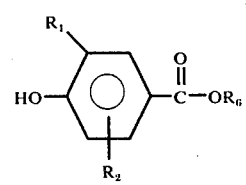

wherein $R_1$ and $R_2$ are as defined above and
$R_6$ is hydrogen, alkyl($C_1$-$C_6$), aralkyl($C_7$-$C_{10}$) or phenyl, to produce a compound of formula If,

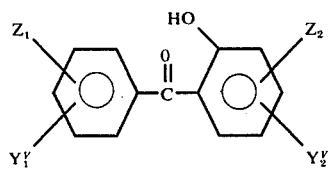

wherein $Z_1$ and $Z_2$ are as defined above, and
$Y_1^V$ and $Y_2^V$ have the significances of $Z_1$ and

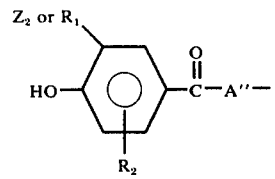

wherein $R_1$, $R_2$ and A'' are as defined above,
wherein at least one of $Y_1^V$ and $Y_2^V$ is

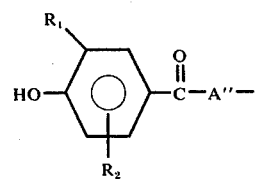

wherein $R_1$, $R_2$ and A'' are as defined above, and when required, converting the resulting compound into the complex of a divalent metal.

The process in accordance with variant (a) above, may, for example, be effected as follows, viz:

The compound of formula III may be dissolved in an inert solvent such as a hydrocarbon solvent, e.g. toluene, benzene, heptane or octane or any ether, e.g.

dimethyl ether, and the compound of formula IV added thereto with stirring. The addition may be effected at a temperature between 0° and 60° C, preferably between 0° and 40° C, especially between 0° and 25° C, e.g. at 5° C. The reaction is preferably effected in the presence of an acid binding agent, particularly tertiary amines e.g. triethylamine, or pyridine. After the reaction components have dissolved, the reaction temperature may be raised, e.g. to the boiling temperature of the reaction mixture under reflux.

The reaction product may be worked up in conventional manner, e.g. by washing the reaction mixture with water, separating off the organic phase, distilling off the organic solvent and recrystallizing the resulting product from a suitable solvent, e.g. ethanol or dioxane.

The process in accordance with variant b) above, may, for example, be effected as follows, viz:

The compound of formula IIIa may be dissolved in an inert solvent such as a hydrocarbon solvent, e.g. toluene, benzene, heptane or octane, or an ether, e.g. dimethyl ether, and the compound of formula V added thereto. The reaction is preferably effected in the presence of an acid catalyst such as sulfuric acid or phosphoric acid. The reaction is preferably effected at an elevated temperature, conveniently at the boiling temperature of the reaction mixture under reflux, e.g. between 90° and 180° C, preferably between 90° and 140° C. When the compound of formula V is in free acid form, the reaction may also be effected in the presence of phosphorus pentachloride or phosphorus trichloride as catalysts, to convert the ester to an intermediate acid chloride.

The metal complex form of the compounds of formula I may be produced from the free phenol form thereof in manner known per se, e.g. by means of the corresponding alkali metal salts prepared by reaction of the free phenolic form of the compounds with an alkali, e.g. sodium hydroxide. The complex is formed by reacting the alkali metal salt form of the compound of formula I with a suitable derivative of the divalent metal such as the chloride e.g. nickel chloride, manganese chloride and zinc chloride.

The compounds of formulae III, IV and V are either known, or, insofar as they are not known, they may be produced in analogous manner to the processes for producing the known compounds or in manner known per se.

The compounds of formula I are useful for stabilizing organic material susceptible to U.V. degradation by a method comprising treating the organic material with a compound of formula I. By the term "treating" is meant either surface coating or incorporation into the body of the organic material, in manner known per se.

The above method also forms part of the present invention.

The method of the invention comprises treating the organic material, either by way of coating the compound of formula I as a film on the surface of the organic material, or by way of mixing the compound of formula I with the organic material, preferably the latter so as to uniformly distribute the compound of formula I throughout the body of the organic material. Thus, according to a first embodiment the method may be effected by intimately mixing the U.V. stabilizer with a particulate form of, for example, a plastics material such as polypropylene, e.g. polypropylene granules, in a kneader or other suitable device, to obtain uniform distribution of the U.V. stabilizer throughout the plastics material. The plastics material may thereafter be formed into final shape, e.g. by extrusion or injection moulding.

According to a second embodiment, organic material in final form, for example, a textile filament, is passed through a dispersion of the U.V. stabilizer, e.g. in aqueous medium, to provide a protective coating of the U.V. stabilizer as a surface film on the organic material. Textile filaments or fabrics of polyethylene terephthalate or cellulose acetate are suited to this mode of application.

According to a third embodiment of the method of the present invention, particularly suited to stabilization of polymers or copolymer susceptible to U.V. degradation, e.g. polypropylene, the U.V. stabilizer is mixed with the monomer or prepolymer before polymerisation or, as the case may be, copolymerisation, is effected, to yield the polymer or copolymer having the U.V. stabilizer uniformly distributed therethrough. The polymer or copolymer may thereafter be extruded, moulded or otherwise formed into final shape.

Examples of organic materials susceptible to U.V. degradation and embraced by the method of the present invention are cellulose derivatives, e.g. cellulose acetate, cellulose acetobutyrate, ethyl cellulose, cellulose nitrate and cellulose propionate, polyalkylenes, e.g. polyethylene and polypropylene, polyvinyl derivatives e.g. polyvinyl chloride, polyvinyl chloride acetate and polyvinyl alcohol, polyamides, polyesters, polyacrylonitrile, polystyrene, silicon rubber, melamineformaldehyde resins, urea-formaldehyde resins, allyl casting resins, polymethylmethacrylate, copolymers such as acrylonitrile - butadiene - styrene copolymers and natural products such as rubber, cellulose, wool and silk.

Stabilized organic materials according to the invention may exist in solid form e.g. panels, rods, coatings, sheets, films, tapes, fibers, granules or powders, or in liquid form, e.g. solutions, emulsions or dispersions.

The organic material may also be treated with other additives, e.g. heat and oxidation stabilizers. Other additives that may be mentioned are 1, 2, 3- triazoles, organic sulphur compounds, tin and trivalent phosphorus compounds and nickel salts of carboxylic acids.

The amount of U.V. stabilizer employed in the method of the present invention will of course vary with the mode of application, the compound employed and the nature of the organic material to be treated. In general, however, satisfactory results are obtained when the amount of U.V. stabilizer employed is between 0.01 and 5%, preferably between 0.05 and 1% of the weight of organic material to be treated.

The compounds of formula I may be employed in formulation form for the stabilization of organic materials, in association with an inert carrier or diluent. Such formulations may be in the form of polishes, creams and lotions, e.g. for surface application to the organic material. Such formulations also form part of the present invention.

An example of the method of the invention will now be described.

METHOD EXAMPLE

Polypropylene granules are homogeneously mixed with 0.5% by weight of a compound of formula I, e.g. the compound of the formula:

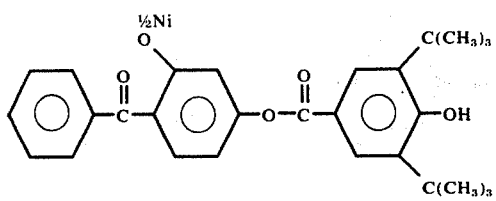

and the mixture kneaded on a roller mill at 180° C. After kneading, the mixture is extruded into foil form of 0.3 mm thickness.

The example is repeated employing polyvinyl chloride instead of polypropylene and 0.5% of a compound of formula I, e.g.

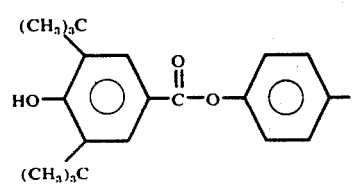

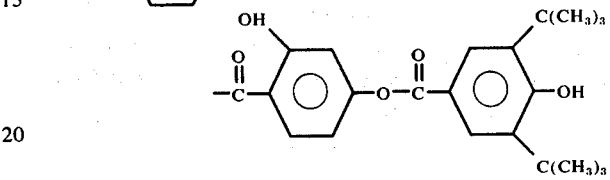

The relative stability of the organic materials to U.V. radiation is found to be increased (De La Rue method in the climate test at 40° C and at 75% relative air humidity).

Examples of the process of the invention will now be described. Where temperatures are referred to, these are in ° C.

EXAMPLE 1

Production of the compound of formula

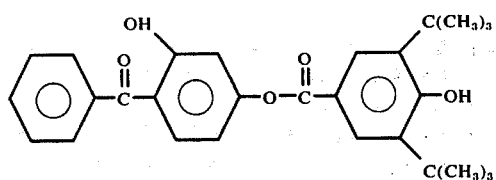

21.4 parts of 2,4-dihydroxybenzophenone and 10.1 parts of triethylamine are fed into 200 parts of toluene. While stirring at 5° C, 26.8 parts of 3,5-di-tertiary butyl-4-hydroxybenzoic acid chloride are added in portions to the solution, and reaction is allowed to continue until no more 2,4-dihydroxybenzophenone is detectable. The mixture is then washed with water, the organic phase separated, dried, and the solvent removed by distillation. The residue is crystallized from ethanol with the addition of decolorizing carbon.

| Analysis | C % | H % | O % |
|---|---|---|---|
| calculated | 75.3 | 6.8 | 17.9 |
| found | 75.1 | 6.8 | 18.0 |

In analogous manner the compounds of formula

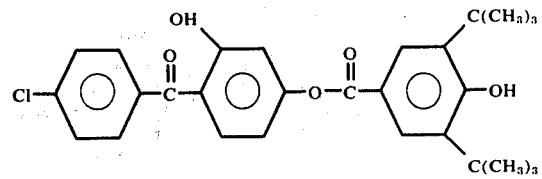

and of formula

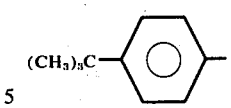

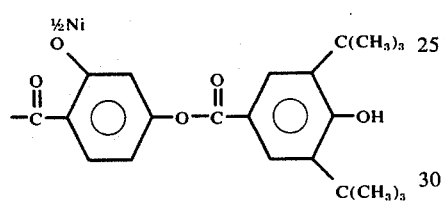

are produced employing 2,4-dihydroxy-4'-chlorobenzophenone or, respectively, 2,4-dihydroxy-4'-di-tertiary-butylbenzophenone.

EXAMPLE 2

Production of the compound of formula 17.7 parts of 2,4-dihydroxy-4'-phenylsulphonylbenzophenone and 4.45 parts of pyridine are fed into 150 parts of toluene. While stirring at room temperature, 13.4 parts of 3,5-di-tertiary-butyl-4-hydroxybenzoic acid chloride is added to the solution and the reaction mixture is allowed to react at reflux until no more acid chloride is shown. The mixture is then washed with water, the organic phase separated, dried, and the solvent is removed by distillation. The residue is crystallized from a mixture of ethanol/dioxane.

| Analysis | C % | H % | S % | O % |
|---|---|---|---|---|
| Calculated | 69.6 | 5.8 | 5.5 | 19.1 |
| found | 69.9 | 5.8 | 5.4 | 19.1 |

EXAMPLE 3

Production of the compound of formula

-continued

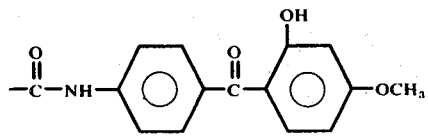

7.29 parts of 2-hydroxy-4-methoxy-4'-aminobenzophenone and 3.03 parts of triethylamine are fed into 250 parts of toluene. While stirring at room temperature, 8.06 parts of 3,5-di-tertiary-butyl-4-hydroxybenzoic acid chloride are added in portions to the mixture which is boiled at reflux until no more acid chloride is detected. The mixture is then cooled, washed with water, the organic phase separated and dried and the solvent removed by distillation. The residue is crystallized from a mixture of ethanol/dioxane.

| Analysis   | C %  | H % | N % | O %  |
|------------|------|-----|-----|------|
| Calculated | 73.3 | 7.0 | 3.0 | 16.8 |
| found      | 73.5 | 7.4 | 2.7 | 17.1 |

EXAMPLE 4

Production of the compound of formula

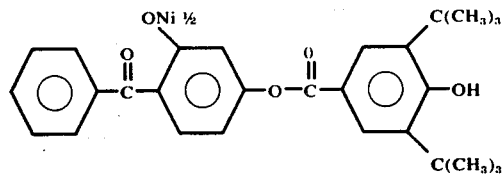

8.9 parts of the compound produced in Example 1 are dissolved in 100 parts of ethanol at 45° C. To this solution is added dropwise at the same temperature a solution of 1.12 parts of KOH in 10 parts of water. Subsequently a solution of 2.36 parts of $NiCl_2\cdot 6H_2O$ in 20 parts of ethanol is added and reaction is allowed to continue for 30 minutes. The green mixture is concentrated by evaporation, water is added and the greenish-yellow precipitate is filtered off by suction, washed with water and dried.

| Analysis   | Ni % |
|------------|------|
| calculated | 6.2  |
| found      | 6.5  |

In analogous manner the nickel complexes of the compounds produced in the Examples 1 to 3 were prepared.

The compounds listed in the following Table were produced in analogous manner to that described in the preceding Examples.

Table

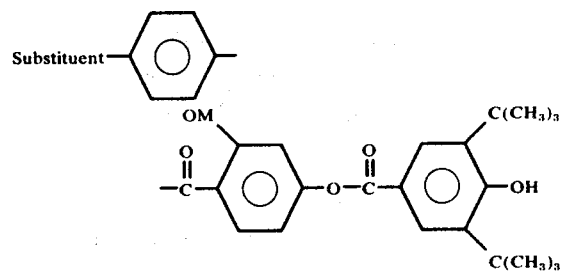

| Ex. No. | M  | Substituent |
|---------|----|-------------|
| 5       | H  | $CH_3-SO_2-$ |
| 6       | Ni |             |
| 7       | H  |             |
| 8       | Ni |             |
| 9       | H  |             |
| 10      | Ni |             |
| 11      | H  | $CH_3-$     |
| 12      | Ni |             |
| 13      | H  | $(CH_3)_3C-$ |
| 14      | Ni |             |

What is claimed is:

1. A compound of the formula:

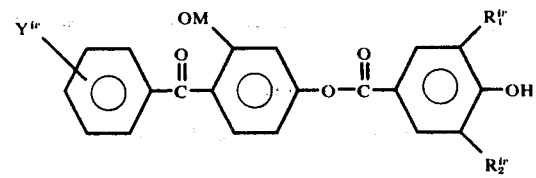

wherein $Y^{iv}$ is hydrogen, fluorine, chlorine, bromine or alkyl of 1 to 9 carbon atoms,
$R_1^{iv}$ is tertiary butyl,
$R_2^{iv}$ is tertiary alkyl of 4 to 9 carbon atoms, and
M is hydrogen, an alkali metal or one equivalent of divalent nickel, zinc, manganese, copper, cobalt, lead, titanium or calcium.

2. A compound according to claim 1 wherein M is hydrogen or one equivalent of divalent nickel, zinc, manganese, copper, cobalt, lead, titanium or calcium.
3. A compound of claim 1, in alkali metal salt form.
4. A compound of claim 3, in sodium salt form.
5. The compound of claim 2, of the formula:

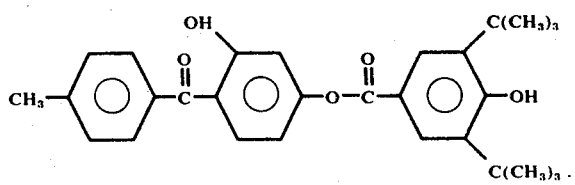

6. The compound of claim 2, of the formula:

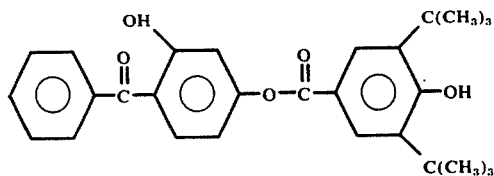
7. The compound of claim 2, of the formula:
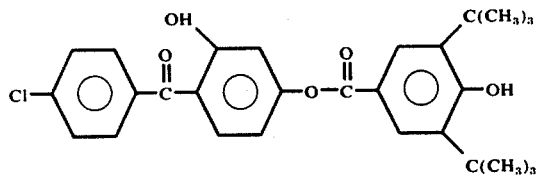
8. The compound of claim 2, of the formula:
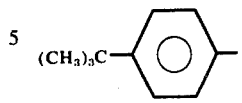
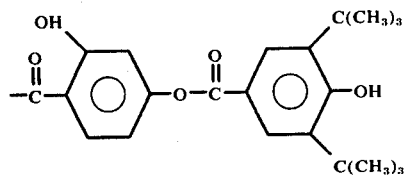
9. A compound of claim 1, in divalent nickel complex form.
* * * * *